US005824835A

United States Patent [19]
Agaskar et al.

[11] Patent Number: 5,824,835
[45] Date of Patent: *Oct. 20, 1998

[54] ISOPARAFFIN-OLEFIN ALKYLATION PROCESS

[75] Inventors: Pradyot A. Agaskar; Tracy J. Huang, both of Lawrenceville, N.J.

[73] Assignee: Mobil Oil Corporation, Fairfax, Va.

[*] Notice: The terminal 5 months of this patent has been disclaimed.

[21] Appl. No.: 383,152

[22] Filed: Feb. 3, 1995

[51] Int. Cl.[6] .............................. C07C 2/58; B01J 29/06
[52] U.S. Cl. ................ 585/722; 502/64; 502/66
[58] Field of Search ............... 585/722; 502/64, 502/66

[56] References Cited

U.S. PATENT DOCUMENTS

| | | | |
|---|---|---|---|
| 2,804,491 | 8/1957 | May et al. | 260/683.4 |
| 3,251,902 | 5/1966 | Garwood et al. | 260/683.64 |
| 3,450,644 | 6/1969 | Lanewala et al. | 252/416 |
| 3,549,557 | 12/1970 | Bolton et al. | 252/455 |
| 3,644,565 | 2/1972 | Biale | 260/683.43 |
| 3,647,916 | 3/1972 | Ceasar et al. | 260/683.43 |
| 3,655,813 | 4/1972 | Kirsch et al. | 260/683.43 |
| 3,706,814 | 12/1972 | Kirsch et al. | 260/683.43 |
| 3,738,977 | 6/1973 | Biale | 260/94.9 DA |
| 3,800,003 | 3/1974 | Sobel | 260/683.49 |
| 3,862,258 | 1/1975 | Huang et al. | 260/683.44 |
| 3,893,942 | 7/1975 | Yang | 252/411 |
| 3,917,738 | 11/1975 | Fenske et al. | 260/683.43 |
| 4,384,161 | 5/1983 | Huang | 585/722 |
| 5,116,794 | 5/1992 | Skeels et al. | 502/85 |

FOREIGN PATENT DOCUMENTS

| | | |
|---|---|---|
| 0 565 197 A1 | 10/1993 | European Pat. Off. . |
| 0 565 198 A1 | 10/1993 | European Pat. Off. . |
| 1593716 | 7/1970 | France . |
| 2631956 | 11/1990 | France . |

*Primary Examiner*—Walter D. Griffin
*Assistant Examiner*—In Suk Bullock
*Attorney, Agent, or Firm*—Thomas W. Steinberg; Malcolm D. Keen

[57] ABSTRACT

The present invention provides a process for alkylating an olefin with an isoparaffin comprising contacting an olefin-containing feed with an isoparaffin-containing feed with a solid catalyst comprising zeolite Beta having a silica:alumina ratio in the as-synthesized state of less than about 18.

7 Claims, No Drawings

ISOPARAFFIN-OLEFIN ALKYLATION PROCESS

FIELD OF THE INVENTION

The present invention relates to the art of improving octane rating of gasoline by alkylating an isoparaffin with an olefin stream. More particularly, the invention relates to the use of a high aluminum zeolite Beta catalyst for isoparaffin-olefin alkylation.

BACKGROUND OF THE INVENTION

Alkylation is a reaction in which an alkyl group is added to an organic molecule. Thus an isoparaffin can be reacted with an olefin to provide an isoparaffin of higher molecular weight. Industrially, the concept depends on the reaction of a $C_2$ to $C_5$ olefin with isobutane in the presence of an acidic catalyst producing a so-called alkylate. This alkylate is a valuable blending component in the manufacture of gasolines due not only to its high octane rating but also to its sensitivity to octane-enhancing additives.

Industrial alkylation processes have historically used hydrofluoric or sulfuric acid catalysts under relatively low temperature conditions. The sulfuric acid alkylation reaction is particularly sensitive to temperature, with low temperatures being favored to minimize the side reaction of olefin polymerization. Acid strength in these liquid acid catalyzed alkylation processes is preferably maintained at 88 to 94 weight percent by the continuous addition of fresh acid and the continuous withdrawal of spent acid. The hydrofluoric acid process is less temperature sensitive and the acid is easily recovered and purified.

Both sulfuric acid and hydrofluoric acid alkylation share inherent drawbacks including environmental and safety concerns, acid consumption, and sludge disposal. Research efforts have been directed to developing alkylation catalysts which are equally as effective as sulfuric or hydrofluoric acids but which avoid many of the problems associated with these two acids. For a general discussion of sulfuric acid alkylation, see the series of three articles by L. F. Albright et al., "Alkylation of Isobutane with $C_4$ Olefins", 27 *Ind. Eng. Chem. Res.,* 381–397, (1988). For a survey of hydrofluoric acid catalyzed alkylation, see 1 *Handbook of Petroleum Refining Processes* 23–28 (R. A. Meyers, ed., 1986).

With the increasing demands for octane and the increasing environmental concerns, it has been desirable to develop an alkylation process employing safer, more environmentally acceptable catalyst systems. Specifically, it is desirable to provide an industrially viable alternative to the currently used hydrofluoric and sulfuric acid alkylation processes. Consequently, substantial efforts have been made to develop a viable isoparaffin-olefin alkylation process which avoids the environmental and safety problems associated with sulfuric and hydrofluoric acid alkylation while retaining the alkylate quality and reliability characteristic of these well-known processes. Research efforts have been directed toward solid as well as liquid alkylation catalyst systems, as reflected in the following references.

U.S. Pat. No. 3,862,258 teaches an alkylation process using a catalyst comprising a macroreticular acid cation exchange resin and boron trifluoride. According to the patent, the life of such a catalyst can be extended by the presence in the reaction mixture of closely controlled amounts of water which can be added to the feed as water or as water-forming compound.

U.S. Pat. No. 3,450,644 discloses a method for regenerating a zeolite catalyst used in hydrocarbon conversion processes involving carbonium ion intermediates.

U.S. Pat. No. 3,549,557 describes alkylation of isobutane with $C_2$–$C_3$ olefins using certain crystalline aluminosilicate zeolite catalysts in a fixed-, moving- or fluidized bed system.

U.S. Pat. No. 3,644,565 discloses alkylation of a paraffin with an olefin in the presence of a catalyst comprising a Group VIII noble metal present on a crystalline aluminosilicate zeolite. The catalyst is pretreated with hydrogen to promote selectivity.

U.S. Pat. No. 3,647,916 describes an isoparaffin-olefin alkylation process featuring use of an ion-exchanged crystalline aluminosilicate, isoparaffin/olefin molar ratios below 3:1 and regeneration of the catalyst.

U.S. Pat. No. 3,655,813 discloses a process for alkylating $C_4$–$C_5$ isoparaffins with $C_3$–$C_9$ olefins using a crystalline aluminosilicate zeolite catalyst wherein a halide adjuvant is used in the alkylation reactor. The isoparaffin and olefin are introduced into the alkylation reactor at specified concentrations and catalyst is continuously regenerated outside the alkylation reactor.

U.S. Pat. No. 3,706,814 discloses another zeolite-catalyzed isoparaffin-olefin alkylation process and further provides for the addition of $C_5$+ paraffins such as Udex raffinate or $C_5$+ olefins to the alkylation reactor feed and the use of specific reactant proportions, halide adjuvants, etc.

U.S. Pat. No. 3,738,977 discloses alkylation of paraffins with ethylene using a zeolite catalyst which possesses a Group VII metal component. The catalyst is pretreated with hydrogen.

U.S. Pat. No. 3,917,738 describes a process for alkylating an isoparaffin with an olefin using a solid, particulate catalyst capable of absorbing the olefin. The isoparaffin and the olefin are admixed to form a reactant stream in contact with catalyst particles at the upstream end of an adsorption zone. Thereafter, the reactants are passed concurrently with the catalyst so that a controlled amount of olefin is adsorbed into the catalyst before the combination of reactants and catalyst is introduced into an alkylation zone. This controlled olefin adsorption is thought to prevent polymerization of the olefin during alkylation.

U.S. Pat. No. 4,384,161 describes a process of alkylating isoparaffins with olefins to provide alkylate using a large-pore zeolite catalyst capable of absorbing 2,2,4-trimethylpentane, for example, ZSM-4, ZSM-20, ZSM-3, ZSM-18, zeolite Beta, faujasite, mordenite, zeolite Y and the rare earth metal-containing forms thereof, and a Lewis acid such as boron trifluoride, antimony pentafluoride or aluminum trichloride. The use of a large-pore zeolite with a Lewis acid is reported to increase the activity and selectivity of the zeolite, thereby effecting alkylation with high olefin space velocity and low isoparaffin/olefin ratio. According to the patent, problems arise in the use of solid catalyst in that they appear to age rapidly and cannot perform effectively at high olefin space velocity and the patent teaches the above solution to rectify the problem utilizing a zeolite alkylation catalyst.

U.S. Pat. No. 2,804,491 relates to an isoparaffin-olefin alkylation to make gasoline at temperatures between −20° and 150° F. utilizing a two-component catalyst comprising essentially excess $BF_3$ with a "silica stabilized gel alumina." No activators are taught.

U.S. Pat. Nos. 3,251,902 and 3,893,942, as well as French Patent 1,593,716 and the article by Kirsh and Potts, DIV. OF PET. CHEM. A.C.S. 15, A109 (1970) address alkylation in the presence of zeolite-based catalyst systems.

U.S. Pat. No. 3,800,003 relates to a process for producing an alkylation reaction product from an isoparaffinic reactant and an olefinic reactant containing 1-butene, 2-butene and isobutene which includes passing the olefinic reactant through an isomerization zone. The isomerization catalyst comprises a crystalline aluminosilicate combined with a substantially anhydrous boron halide which can be boron trifluoride. Conventional catalysts are utilized for the alkylation reaction and include sulfuric acid and hydrogen fluoride catalyst which have the disadvantages set forth above.

The two-part article "Modern Alkylation", by Lyle F. Albright, published in the Nov. 12 and 26, 1990 issues of the *Oil and Gas Journal* summarizes the present state of $H_2SO_4$ and HF alkylation technology.

While it would be desirable to substitute a solid alkylation catalyst for the liquid catalysts described above, solid catalysts have not proven in the past to be commercially viable alternatives to liquid acid catalysts due to problems with catalyst longevity and alkylate product quality.

More specifically, the use of conventional zeolite Beta (synthesized in the presence of monovalent metal cations) for isobutane alkylation has been considered (FR 2,631,956; EPA 0,565,197 A1; and EPA 0,565,198 A1), but the alkylate products reportedly obtained from these processes have not proven to be commercially acceptable substitutes for alkylates produced by conventional HF- or $H_2SO_4$-catalyzed alkylation processes.

SUMMARY OF THE INVENTION

The present invention includes a process for alkylating an olefin with an isoparaffin comprising contacting an olefin-containing feed with an isoparaffin-containing feed with a crystalline microporous material.

The present concept deals with the use of high aluminum zeolite Beta catalysts for isoparaffin-olefin alkylation. The high aluminum zeolite-Beta is hydrothermally synthesized, typically in the presence of tetraethylammonium hydroxide (or tetraethylammonium bromide) and at least one divalent metal cation such as $Ba^{++}$ and $Ca^{++}$. The high aluminum zeolite Beta used in the present process produces better alkylate quality than conventional zeolite Beta which is hydrothermally synthesized in the presence of tetraethylammonium hydroxide (or tetraethylammonium bromide) and a monovalent metal cation such as $Na^+$. The catalyst may optionally contain a hydrogenation metal component (such as Pt and Pd) which can be incorporated by impregnation or exchange. The addition of a hydrogenation metal component is particularly desirable if the catalyst is to be hydrogenatively (rather than oxidatively) regenerated. The alkylate produced by the present process is useful as octane blending stock for the manufacturing of reformulated gasoline.

The high aluminum zeolite Beta materials are preferably prepared by a method that involves a predigestion step during which a mixture consisting of tetraethylammonium hydroxide and sources of silica and alumina is maintained at about 100° C. for several hours at which time a clear transparent solution is obtained. At the end of this step a solution containing soluble salts of divalent metal cations such as calcium and barium is added and the resulting gel is heated with stirring at temperatures below 200° C. for a period of time until crystallization is completed. The as synthesized products are converted to the acid form by first exchanging the divalent metal ions with ammonium ions followed by calcination. The high aluminum zeolite Beta can also be synthesized without a predigestion step; in this case, the mixture containing all the necessary components including divalent cations is heated with stirring at temperature below 200° C. for a period of time until crystallization is completed. Preferably, the Si/Al ratio of the as-synthesized zeolite-Beta is less than 18. More preferably, the Si/Al ratio is less than 10.

Light olefins such as ethylene, propylene, butene, pentene, hexene, or mixtures thereof are useful as feedstock olefins. Hydrocarbon streams containing a mixture of paraffins and olefins such as FCC butane/butene stock can also be employed. The isoparaffin/olefin (I/O) ratio in the feed can range from 1:1 to 100:1. An internal I/O of above 500 in the reactor is desirable, but above 1000 or higher is preferable. The high internal I/O ratio can be achieved by recycle of part of the reactor effluent or by back-mixing of the reactor content. Alkylation can be conducted in liquid phase, or critical fluid phase, or vapor phase, using fixed-bed, or moving-bed, or slurry reactor. Operating pressure can range from about 0 to about 2000 psig. When liquid phase is employed, the operating pressure is high enough to keep the reactants in liquid phase. Operating temperature can range from about 0° C. to about 500° C., preferably below 300° C. Olefin weight hourly space velocity can range from 0.01 to 10 $hr^{-1}$. The deactivated catalyst can be oxidatively regenerated. If the catalyst is to be hydrogenatively regenerated, the catalyst preferably contains at least one hydrogenation metal component such as Pt or Pd.

DETAILED DESCRIPTION

The process of the invention converts a feedstock containing at least one isoparaffin having from 4 to 8 carbon atoms and at least one olefin having from 2 to 12 carbon atoms to a product stream containing a higher molecular weight isoparaffin.

Feedstocks

Feedstocks useful in the present alkylation process include at least one isoparaffin and at least one olefin. The isoparaffin reactant used in the present alkylation process has from about 4 to about 8 carbon atoms. Representative examples of such isoparaffins include isobutane, isopentane, 3-methylhexane, 2-methylhexane, 2,3-dimethylbutane and 2,4-dimethylhexane.

The olefin component of the feedstock includes at least one olefin having from 2 to 12 carbon atoms. Representative examples of such olefins include butene-2, isobutylene, butene-1, propylene, ethylene, hexene, octene, and heptene, merely to name a few. The preferred olefins include the $C_4$ olefins, for example, butene-1, butene-2, isobutylene, or a mixture of one or more of these $C_4$ olefins, with butene-2 being the most preferred. Suitable feedstocks for the process of the present invention are described in U.S. Pat. No. 3,862,258 to Huang et al. at column 3, lines 44–56, the disclosure of which is incorporated by reference as if set forth at length herein.

Isoparaffin:olefin ratios in the reactor feed typically range from about 1.5:1 to about 100:1 to produce a high-octane isobutane:butene alkylate product at industrially useful yields. Higher isoparaffin:olefin ratios may also be used, however limited availability of produced isoparaffin within the refinery coupled with the relatively high cost of purchased isoparaffin favor isoparaffin:olefin ratios within the ranges listed above.

Process Conditions

The present alkylation process is suitably conducted at temperatures from about 0° C. up to about 500° C., preferably below about 300° C.

Hydrocarbon flow through the alkylation zone containing the catalyst is typically controlled to provide olefin weight hourly space velocity (WHSV) sufficient to convert about 99 percent by weight of fresh olefin to alkylate product. Typical WHSV values fall within the range of from about 0.01 to about 10 hr$^{-1}$, preferably from about 0.01 to about 5 hr$^{-1}$.

The particular operating conditions used in the present process will depend on the specific alkylation reaction being effected. Process conditions such as temperature, pressure, space velocity and molar ratio of the reactants will effect the characteristics of the resulting alkylate, and may be adjusted within the disclosed ranges by those skilled in the art with only minimal trial and error.

Catalysts

Zeolite Beta is generally taught in U.S. Pat. No. 3,308,069 which is incorporated herein by reference.

The structure of zeolite-beta has been determined and is described in the publications by J. B. Higgins et al. (Zeolite 1988, 8, 446–452) and J. M. Newsam et al. (Peoc. R. Soc. Lond. A 1988, 420, 375–405).

The catalyst useful in the present invention is a high alumina zeolite Beta having a silica:alumina ratio of less than about 18, preferably less than about 10. The zeolite may be composited with one or more inorganic oxides, examples of which include, but are not limited to, alumina, silica, boria, oxides of phorphorus, titania, zirconia, chromia, zinc oxide, magnesia, calcium oxide, silica-alumina, silica-magnesia, silica-alumina-magnesia, silica-alumina-zirconia, as well as the naturally occurring inorganic oxides of various states of purity such as bauxite, clay, diatomaceous earth, merely to name a few. The preferred inorganic oxide binders are silica, alumina and zirconia.

EXAMPLE 1

A silica source, colloidal silica 30% w/w (30.19 g), was added to the stainless steel bottom pot of a 300 mL capacity autoclave from Parr Instrument Co. that had been filled with 33.81 g of a 35% aqueous w/w solution of tetraethylammonium hydroxide solution. Aluminum trihydroxide (1.4474 g) was then added to this mixture followed by 0.04 g water. The thin milky white solution was heated in the autoclave to 100° C. at 2° C. per minute while being stirred at 60 rpm and held for 48 hours. The autoclave was opened and a mixture consisting 31.70 g of a 5% w/w aqueous solution of barium hydroxide octahydrate and 2.82 g of a 10% w/w aqueous potassium hydroxide was then added. The mixture was then reheated to 150° C. at 2° C. per minute and held for 168 hours with stirring at 60 rpm. The product was collected on filter paper and dried in an oven at 110° C. in a stream of air. This was treated with a 1M ammonium chloride solution whose pH had been adjusted to 8 for 1 hour at 60° C. This treatment was repeated two more times and the exchanged product dried at 110° C. in a stream of air. The dry exchanged product was placed in a shallow dish and heated in a tube furnace up to 538° C. in a stream of dry nitrogen at 2° C. per minute and held for 3 hours. The temperature was lowered to 250° C. and the atmosphere was switched to air after which the temperature was raised again to 538° C. at 2° C. per minute and held for three hours. The product on cooling was the H-form of the catalyst with the compositional parameters Si/Al=7.3; Ba/Al=0.06; K/Al=0.03. The X-ray diffraction pattern was that of a highly crystalline zeolite Beta. This catalyst is called Catalyst A.

EXAMPLE 2

A silica source, AEROSIL-200 (14.82 g), was added to a beaker containing 72.63 g of a 25% w/w aqueous solution of tetraethylammonium hydroxide and the mixture stirred for 30 minutes to obtain a very viscous slurry. To this was added 3.35 g of aluminum tris-isopropoxide and the mixture stirred for an additional 90 minutes to obtain a moderately viscous pourable slurry. This was placed directly in the stainless steel pot of a 300 mL capacity autoclave from Parr Instrument Co. and the beaker washed with 9.10 g of water which was also added to the autoclave pot. The temperature was raised to 100° C. at 2° C. per minute and held for 20 hours while stirring at 60 rpm. A 10% w/w aqueous solution of calcium chloride dihydrate weighing 12.09 g, was taken in a pressurized liquid addition bomb and dropped into the autoclave pot while the stirring rate was increased to 300 rpm. After 5 minutes the stirring rate was reduced to 60 rpm and the temperature raised to 150° C. at 2° C. per minute and held for 168 hours. The autoclave was opened and the milky white contents filtered through a filter paper. The solid was washed with 100 mL of distilled water and then dried in an oven maintained at 110° C. with a stream of air. The white product was heated in a shallow dish in a tube furnace first in dry nitrogen atmosphere up to 538° C. at 2° C. per minute and held for 3 hours before being cooled to 250° C. The atmosphere was then switched to air and the product reheated to 538° C. at 2° C. per minute and held for three hours. The calcined product was treated with a 1M solution of ammonium chloride whose pH had been adjusted to about 8 with ammonium hydroxide for 1 hour. This treatment was repeated two more times and the resultant product was calcined as described earlier. The final product was the hydrogen form of the catalyst with the composition ratios Si/Al=16; Ca/Al=0.2. The X-ray pattern was that of highly crystalline zeolite Beta. This catalyst is called Catalyst B.

EXAMPLE 3

35.5 parts of sodium hydroxide, 5.4 parts of aluminum sulfate, and 48.5 parts of tetraethylammonium bromide were sequentially added to 116.9 parts of water with stirring. After that, 29.5 parts of silica and 1 part of zeolite Beta seeds were subsequently added to the mixture. The crystallizer was then closed and heated to 138° C. After 76 hours, the crystallizer was cooled to 110° C.; the vessel was then flashed to remove any volatile organics. Upon further cooling to 77° C., the slurry was transferred to a decanter where flocculation was carried out. After three decantations were completed, the slurry was NH$_4$NO$_3$ washed three times to further reduce the sodium level. The as-synthesized zeolite material was filtered. The total product collected was 25.7 parts. The analysis of this material showed 0.03 wt % Na and 82.2 wt % ash. The composition of this material gave a Si/Al ratio of 18.5 (or a SiO$_2$/Al$_2$O$_3$ ratio of 37). The x-ray pattern was that of highly crystalline zeolite Beta. The product was heated in a shallow dish in a tube furnace first in dry nitrogen atmosphere up to 538° C. at 2° C. per minute and held for 3 hours before being cooled to 250° C. The atmosphere was then switched to air and the product reheated to 538° C. at 2° C. per minute and held for three hours. This calcined catalyst is called Catalyst C.

EXAMPLE 4

The Catalysts A, B, and C prepared in Examples 1, 2, and 3 were evaluated in the alkylation of isobutane with butene-2 conducted in a continuous stirred tank reactor. Prior to the testing, catalysts were crushed to <100 mesh and pretreated at 400° C. for 3 hours in dry air. Then 5.35 grams of the catalyst was placed in a 300 cc stainless steel stirred autoclave and the reactor was filled with isobutane. The slurry was stirred at 1900 rpm and heated to 52° C. The pressure was kept at 300 psig. After the desired temperature was reached, a feed with an isobutane/butene-2 ratio of 20/1 was continuously fed into the reactor at a butene weight hourly space velocity of 0.13. On-line samples were taken at various times on stream for the gas chromatographic analysis. After 2.5 hours on stream with Catalyst A, the conversion of butene was 100% and the $C_5+$ alkylate yield was 2.0 g $C_5+$ per g of butene converted. The $C_5+$ alkylate contained 10.9 wt % of $C_5$–$C_7$, 84.3 wt % of $C_8$, and 4.7 wt % of $C_9+$. The TMP/($C_8$-TMP) ratio in the $C_8$ fraction of 11.7. The TMP/($C_8$-TMP) ratio is the ratio of trimethylpentanes to the remaining fraction in the total $C_8$'s. (The remaining fraction contains dimethylhexanes, methylheptanes and n-octane). Thus, the higher the TMP/($C_8$-TMP) ratio, the higher the alkylate octane number and the higher the alkylate quality. The TMP/($C_8$-TMP) ratio as a function of time on stream are shown in Table 1 for comparison among the three catalysts tested.

TABLE 1

| EXAMPLE | 1 | 2 | 3 |
|---|---|---|---|
| Catalyst | A | B | C |
| Metal Cations in the Synthesis Mixture | $Ba^{+2}$ | $Ca^{+2}$ | $Na^+$ |
| Si:Al ratio | 7.3 | 16.0 | 18.5 |
| Alkylate Quality: | | | |
| TMP/($C_8$-TMP) @ 2.5 hr on stream | 11.7 | 9.0 | — |
| TMP/($C_8$-TMP) @ 3.0 hr on stream | — | — | 5.0 |
| TMP/($C_8$-TMP) @ 5.0 hr on stream | 10.8 | 7.6 | — |

Clearly, Catalysts A and B, which were synthesized in the presence of divalent cations, gave better alkylate quality than Catalyst C, which was synthesized in the presence of monovalent cations.

EXAMPLE 5

EPA 0,565,198 A1 disclosed that a zeolite Beta with a $SiO_2/Al_2O_3$ ratio of 12.7 gave a TMP/($C_8$-TMP) ratio of 3.5 at 80°–90° C. with I/O=30. The zeolite Beta sample in the '198 application was prepared by treating a conventional zeolite Beta (synthesized in the presence of Na+) with sodium hydroxide solution to reduce the $SiO_2/Al_2O_3$ ratio. U.S. Pat. No. 2,631,956 disclosed a conversion in which conventional zeolite Beta with a $SiO_2/Al_2O_3$ ratio of 28 (Si/Al=14) gave a TMP/(C8-TMP) ratio of only 1.2–1.7 at 80° C. with I/O=10. When our Catalyst A ($SiO_2/Al_2O_3$= 14.6) was tested at 85° C. with I/O=20, the TMP/($C_8$-TMP) ratio was 6.8. Again clearly, Catalysts A of the present invention, which was synthesized in the presence of divalent cations, gave better alkylate quality than those conventional zeolite Beta catalysts, which were synthesized in the presence of monovalent cations.

What is claimed is:

1. A process for alkylating an olefin with an isoparaffin comprising contacting an olefin-containing feed with an isoparaffin-containing feed with a solid catalyst comprising zeolite Beta having been synthesized in the presence of at least one divalent metal cation and having a Si/Al ratio in the as-synthesized state of less than about 18.

2. The process of claim 1 wherein said Si/Al ratio is less than about 10.

3. The process of claim 1 wherein said metal cation is selected from the group consisting of $Ba^{++}$ and $Ca^{++}$.

4. The process of claim 1 wherein said zeolite Beta has been synthesized in the presence of tetraethylammonium hydroxide or tetraethylammonium bromide.

5. The process of claim 1 wherein said zeolite Beta has been synthesized by the steps of:

(a) predigesting a mixture consisting of tetraethylammonium hydroxide, at least one source of silica and at least one source of alumina to obtain a first aqueous solution;

(b) adding divalent metal cations to said first aqueous solution of step (a) to form a second aqueous solution; and (c) crystallizing zeolite Beta from said second solution.

6. The process of claim 1 wherein the solid catalyst further comprises a hydrogenation metal component which is incorporated into said solid catalyst by impregnation or ion-exchange.

7. The process of claim 6 wherein the hydrogenation metal component is selected from the group consisting of platinum and palladium.

* * * * *